United States Patent [19]

Simon et al.

[11] 4,423,027
[45] Dec. 27, 1983

[54] PHARMACEUTICAL COMPOSITIONS OF DEGLYCYRRHIZINATED LICORICE (DGL)

[76] Inventors: Lionel N. Simon, 11772 Las Palmas, Santa Ana, Calif. 92705; Kameron W. Maxwell, 24671 Acropolis St., Mission Viejo, Calif. 92691

[21] Appl. No.: 452,085

[22] Filed: Dec. 22, 1982

[51] Int. Cl.³ .......................... A61K 9/28; A61K 9/36
[52] U.S. Cl. .......................................... 424/16; 424/35
[58] Field of Search ................... 424/16, 35

[56] References Cited

U.S. PATENT DOCUMENTS

| | | | |
|---|---|---|---|
| 3,692,896 | 9/1972 | Tsumura et al. | 424/78 |
| 3,917,821 | 11/1975 | Manes | 424/125 |
| 3,929,988 | 12/1975 | Barth | 424/49 |
| 3,940,381 | 2/1976 | Boissevain | 424/180 |
| 4,127,645 | 11/1978 | Witzel et al. | 424/16 |
| 4,163,067 | 7/1979 | Hartung | 260/236.5 |
| 4,229,466 | 10/1980 | Miyazaki et al. | 424/279 |

FOREIGN PATENT DOCUMENTS 2037719  3/1971  Fed. Rep. of Germany .

OTHER PUBLICATIONS

Rees et al. Scand. J. Gastroenterol 14(5):605–607(1979); GA.92 584T.
Baas et al. Z. Gastroenterol 14(2): GA. 90:66845u.
Baas et al. Verh. Dtsch. 685, Inn. Med. 81: 1239–1241(1975); GA.84 1450114.
Bennett et al. J. Pharm. Pharmacol. 32(2):151(1980); GA.93 19117k.
Lahiri et al. East Pharm. 23(268):191–3(1980); GA.94 52816F.
Van Marle et al. Eur. J. Pharmacol. 72(2–3)2-19–225(1981): GA.95: 73729R.
Datla et al. Indian J. Physiol. Pharmacol. 25(1):59–63(1981): GA.95: 175658J.

Primary Examiner—Shep K. Rose
Attorney, Agent, or Firm—Cushman, Darby & Cushman

[57] ABSTRACT

A new solid or liquid dosage form containing deglycyrrhizinated licorice (DGL) has been designed. This form is more suitable for administration to humans than the form previously used because:

(1) irritating ingredients, previously included, possessing no activity, have been removed, (2) bulky, ineffective quantities of antacids have been removed, thereby allowing the amount of the active ingredient DGL to be increased per unit, reducing the number of units needed to be consumed (e.g. from 8 to 4 per day), (3) dangerous, neurotoxic ingredients have been removed, and (4) the bitter DGL has been formulated into an acceptable pharmaceutical dosage form that does not need to be chewed because, unlike other formulations, this formulation is formulated in a novel way that allows for complete and rapid disintegration, releasing the active ingredient in a fashion superior to chewing.

17 Claims, No Drawings

PHARMACEUTICAL COMPOSITIONS OF DEGLYCYRRHIZINATED LICORICE (DGL)

BACKGROUND OF THE INVENTION

This invention relates to a stable, novel formulation of the bitter-tasting deglycyrrhizinated licorice (DGL) which can be formulated to contain other ingredients known as pharmaceutical excipients that will enhance the dissolution and disintegration of the active ingredient, DGL, thereby making it unnecessary to chew tablets containing the DGL. These improved formulations can be swallowed and rapid and complete disintegration in the gastrointestinal tract can be achieved in order to release the ulcer-healing ingredient, DGL.

Licorice has been used for many years in the treatment of gastric disorders. In recent times the serious side effects of licorice became a major drawback to its use and in 1950 it was discovered that the constituent causing the major disturbance was glycyrrhizinic acid.

In the early 1950's it was decided to try and remove this ingredient and in 1952 a report appeared in Munchen Medizinische Wochenschrift by Dr. Irte that tablets of Caved-S were being used in treatment of peptic ulcers. This preparation (Caved-S) contained Bismuth Subnitrate (now known to be neurotoxic) and three other ingredients were used as flavoring or aromatic agents, *Rhamni frangula cortex, Calami rhizoma* and *Foeniculi fructus*. These latter two agents are described as being aromatic and irritants to the bowel. The DGL was prepared by a method which was described in Zagt U.S. Pat. No. 3,046,195.

Caved-S has the formulation:

| | |
|---|---|
| (1) Succ licorice deglycyrrhizinate (DGL) | 0.38 gram |
| (2) Bismuth subnitrate | 0.10 gram |
| (3) Aluminum hydroxide | 0.10 gram |
| (4) Magnesium subcarbonate | 0.20 gram |
| (5) Sodium bicarbonate | 0.10 gram |
| (6) *Calami rhizoma* | 0.01 gram |
| (7) *Rhamni frangula* cortex | 0.03 gram |
| (8) *Foeniculi fructus* | 0.02 gram |
| (9) Excipients q.s. ad. | |

This mixture is formulated as an uncoated tablet to be chewed and taken as 2 tablets on the average of 4 times per day. It is a dark brown, mottled tablet with the bitter taste of unsweetened licorice.

Several recent reports of studies using DGL indicated that the inclusion of antacids was not a necessary component to heal ulcers in laboratory animals and furthermore, that adequate dispersion of the DGL was necessary (capsules of DGL alone were not as effective clinically). In one study it was described that 7 patients out of 17 discontinued taking the medication because of the bitter taste of chewable tablets. In fact, the necessity of chewing 8 tablets a day is a real deterrent to patients taking the medication. It is a well-known fact that patient compliance drops dramatically with the increase in the number of tablets that have to be consumed. Several components of the current formulation, i.e. bismuth salts and aluminum compounds have recently been shown to have neurotoxic side effects.

Recent studies have demonstrated profound healing effects of DGL alone in rats who have aspirin (ASA), stress or restraint induced ulcers. Furthermore, in spite of recent clinical data demonstrating clinical effects of the current DGL formulation that are comparable to or better than cimetidine and ranitidine Caved-S sales have fallen over 90% in the last 5 years concurrent with the availability of tagamet, a product that is a tasteless tablet to be swallowed 4 times a day. In summary, because of a constellation of drawbacks, including drawbacks 1-4 listed below, the current formulation of DGL, while possessing reasonable clinical activity for treating peptic ulcers, is both a medical and marketing failure.

Drawbacks of Caved-S (1) There is a low quantity of active ingredient (DGL) per tablet, thereby necessitating a large (8) number of tablets to be taken daily.

(2) There is the presence of a large quantity of inactive ingredients per tablet, thereby making it impossible to adequately increase the amount of active ingredient and also there is a combination of many ingredients making it difficult to obtain FDA approval.

(3) The active ingredient is bitter and unpleasant in taste and must be chewed in order to disperse the DGL property. (4) Inert ingredients are present that are potentially harmful.

| Ingredients | Side Effect |
|---|---|
| (a) Bismuth Salts | Neurotoxicity |
| (b) Aluminum compounds | Neurotoxicity |
| (c) *Rhamni frangula* cortex | Gastric Irritant |
| (d) *Calami rhizoma* | Gastric Irritant |
| (e) *Foeniculi fructus* | Gastric Irritant |

Because of the above defects there is a need for a novel formulation of DGL that is designed to overcome each of the drawbacks; thereby, producing a medically and commercially viable product taking advantage of the desirable properties of DGL in treating gastric ulcers, duodenal ulcers, and other forms of ulcers.

SUMMARY OF THE INVENTION

The present invention is directed to stable, oral forms of DGL that are pharmaceutically acceptable and overcome either all or most of the inherent drawbacks set forth as items 1 to 4 above of the current commercial form of DGL (Caved-S). These drawbacks are remedied in one single formulation according to the invention to provide DGL in an orally acceptable tablet form or they can be remedied singly or in combination, thus partially correcting the drawbacks of the current commercial product (Caved-S).

Unless otherwise indicated all parts and percentages are by weight.

The composition can consist essentially of or consist of the stated materials.

DETAILED DESCRIPTION

Example 1 (Preferred Formulation)

| | | Quantity/Tab (mg) | Range |
|---|---|---|---|
| 1. | DGL (active ingredient) | 760 | 712–798 |
| 2. | Lactose (inert diluent) | 92.5 | 50–150 |
| 3. | Explotab* (disintegrant) | 9 | 2–12 |
| 4. | Polyvinylpyrrolidone (binder) | 23 | 10–40 |
| 5. | Alcohol, Isopropyl (solvent) | q.s | |
| 6. | Magnesium Stearate (lubricant) | 6.75 | 4.5–10 |
| 7. | Explotab* (disintegrant) | 9 | 2–12 |

-continued

| | Quantity/Tab (mg) | Range |
|---|---|---|
| Total Tab. Wt. | 900.25 | 780.5–1022 |

*Explotab = Sodium Starch Glycolate NF XV

Procedure

Thoroughly mix 1, 2, and 3 in a suitable mixer. Dissolve 4 in 5. With the mixer running slowly add the solution of 4 in 5 to the mixture of 1, 2, and 3. Mix until a uniform wetted mass is obtained and add an additional quantity of 5 if necessary. Place the wet granulation in a drying oven or fluid bed dryer and dry at 42° C. for approximately 4 hours or until no residual alcohol is present. Pass the dried material through a suitable stainless steel screen (approximately 12 mesh Tyler) having connected therewith a milling machine for comminuting. Place the milled material in a suitable blender. Blend for 5 minutess. Stop the blending and add 6 and 7 and blend for an additional 2 minutes. Compress the tablets on a rotary tablet press using suitable tooling.

Other disintegrants can be used besides Explotab, such as Primogel (see explotab) or Avicel (microcrystalline cellulose) in the appropriate quantity (between 1–8% by wt. of explotabs and 5–15% of Avicel), as long as the same procedure specified here is utilized, i.e. there is included some of the disintegrant in the initial wet granulation preparation and there is included some of the disintegrant in the outer core of the granulation mass. The purpose of using this procedure is to produce a tablet that will release the active ingredient, DGL, in a particle size range that is nearly identical to the particle size of the input active ingredient (DGL) without having to chew the bitter tasting tablet. Other disintegrants like sodium alginate, clays and ion exchange resins in the appropriate amounts 2–5%, 5–10% and 0.5–5.0% respectively can be used.

Other pharmaceutically acceptable binders can be used in place of polyvinyl pyrrolidine, e.g. avicel, starch.

Other pharmaceutically acceptable lubricants can be used in place of magnesium stearate, e.g. stearic acid, talc, corn starch and hydrogenated vegetable oils.

Coated tablets are produced in order to mask the taste and color of the active ingredient and to make it easier for the patient to swallow. The taste must be masked for reasons of compliance of the patient in taking the medicine and the color masked for the purposes of making the tablet pharmaceutically acceptable and a second benefit is that it will allow for the production of a comparative placebo tablet.

The tablets are then coated with a thin film of protective material which will dissolve in the stomach or intestine. A typical formulation is given below:

FORMULA FOR FILM COATING OF TABLETS

Formula

| Ingredients | Percent (w/w) |
|---|---|
| Methocel 60 HG* Premium 15 cps | 3.95 |
| Polyethylene Glycol 8000 | 0.55 |
| Water | 92.18 |
| Opaspray** Color Concentrates | 3.32 |

*Methocel 60 HG = Hydroxypropylmethylcellulose
**Opaspray is a trademark for a color concentrate containing: FD & C Lakes, Titanium dioxide and Plasdone (polyvinylpyrrolidone) in a water alcohol base.

DRY WEIGHT OF FILM APPLIED TO TABLETS USNG ABOVE PROCESS AND FORMULA

| Ingredients | Weight (mg) |
|---|---|
| Methocel 60 HG Premium 15 cps | 7.0 |
| Polyethylene Glycol 8000 | 0.9 |
| Opaspray Color Concentrate | 2.1 |

EXAMPLE 2

| | Ingredients | Quantity/Tab (mg) | Range |
|---|---|---|---|
| 1. | DGL (active ingredient) | 760 | 712–798 |
| 2. | Dicalcium Phosphate (diluent) | 92.5 | 50–150 |
| 3. | Explotab (disintegrant) | 9 | 2–12 |
| 4. | Polyvinylpyrrolidone (binder) | 23 | 10–40 |
| 5. | Alcohol, Isopropyl (solvent) | q.s | |
| 6. | Magnesium Stearate (lubricant) | 6.75 | 4.5–10 |
| 7. | Explotab | 9 | 2–12 |
| | Tablet Wt. | 900.25 | 780.5–1022 |

The above formulation also is converted to a coated tablet using the same film coating system and procedure in Example 1.

EXAMPLE 3

The process of microencapsulation is also well known for overcoming the objections to taste and color in pharmaceutical preparations that have problems of taste and color. Because of this a formulation is proposed which would contain DGL formulated as beads, microencapsulated and suspended so that a suitable concentration can be obtained that will allow for the administration of DGL, as a tasteless or pleasant tasting liquid.

Because there is no need to employ the large amounts of excipients and the other materials present in Caved-S, it is possible to increase the dosage of DGL in each tablet. Consequently it is only necessary to administer 4 tablets (and in some cases only 3 tablets) per day rather than the 8 tablets per day required with Caved-S.

What is claimed is:

1. A tablet suitable for treating gastric or duodenal ulcers consisting essentially of an inner core containing deglycyrrhizinated licorice, a pharmaceutically acceptable disintegrant and an outer core including a pharmaceutically acceptable disintegrant, and a pharmaceutically acceptable coating of a film capable of being removed in the gastrointestinal tract.

2. A tablet according to claim 1 having a weight, exclusive of the thin film of 780.5 to 1022 mg and containing 712 and 798 mg of the deglycyrrihizinated licorice.

3. A tablet according to claim 2 which has a weight including the thin layer of 790.5 to 1032 mg.

4. A tablet according to claim 1 wherein the inner core consists essentially of deglycyrrhizinated licorice, a diluent, a disintegrant and a binder and the outer core consists essentially of a disintegrant and a lubricant.

5. A tablet according to claim 3 wherein the tablet, exclusive of the thin film has a weight of 780.5 to 1022 mg and contains in the inner core 712 to 798 mg of deglycyrrihizinated licorice, 50–150 mg of diluent, 2 to 12 mg of disintegrant, and 10 to 40 mg of binder and the outer core consists essentially of 4.5 to 10 mg of lubricant and 2 to 12 mg of disintegrant.

6. A tablet according to claim 5 wherein in the inner core the diluent is lactose or dicalcium phosphate, the disintegrant is sodium starch glycolate and the binder is polyvinyl alcohol and in the outer core the disintegrant is sodium starch glycolate and the lubricant is magnesium stearate.

7. A tablet according to claim 6 wherein the inner core consists of:

| | |
|---|---|
| deglycyrrhizinated licorice | 760 mg |
| lactose | 92.5 mg |
| sodium starch glycolate | 9 mg |
| polyvinylpyrrolidone | 23 mg |
| and the outer core consists of | |
| magnesium stearate | 6.75 mg |
| sodium starch glycolate | 9 mg. |

8. A tablet according to claim 7 wherein the thin coating consists of:

| | |
|---|---|
| hydroxypropylmethyl cellulose | 7.0 mg |
| polyethylene glycol 8000 | 0.9 mg |
| color concentrate suitable to mask the color of the deglycyrrhizinated licorice. | 2.1 mg |

9. A tablet according to claim 6 wherein the inner core consists of:

| | |
|---|---|
| deglycyrrhizinated licorice | 760 mg |
| dicalcium phosphate | 92.5 mg |
| sodium starch glycolate | 9 mg |
| polyvinylpyrrolidone | 23 mg | and the outer core consists of:

| | |
|---|---|
| magnesium stearate | 6.75 mg |
| sodium starch glycolate | 9 mg |

10. A tablet according to claim 9 wherein the thin coating consists of:

| | |
|---|---|
| hydroxypropylmethyl cellulose | 7.0 mg |
| polyethylene glycol 8000 | 0.9 mg |
| color concentrate suitable to mask the color of the deglycyrrhizinated licorice. | 2.1 mg |

11. A tablet according to claim 6 wherein the thin coating consists essentially of hydroxypropylmethyl cellulose and a high molecular weight polyethylene glycol and a colorant suitable to mask the color of the deglycyrrhizinated licorice.

12. A tablet according to claim 5 wherein the thin coating consists essentially of hydroxypropylmethyl cellulose and a high molecular weight polyethylene glycol and a colorant suitable to mask the color of the deglycyrrhizinated licorice.

13. A method of treating a gastric or duodenal ulcer comprising feeding a patient having such an ulcer a tablet according to claim 6.

14. A method of treating a gastric or duodenal ulcer comprising feeding a patient having such an ulcer a tablet according to claim 5.

15. A method of treating a gastric or duodenal ulcer comprising feeding a patient having such an ulcer a tablet according to claim 1.

16. A method of treating a gastric or duodenal ulcer comprising feeding a patient having such an ulcer the microencapsulated product by claim 13.

17. A method of treating a gastric or duodenal ulcer comprising feeding a patient having such an ulcer the microencapsulated product by claim 14.

* * * * *